(12) United States Patent
Futatsuyama et al.

(10) Patent No.: US 9,943,238 B2
(45) Date of Patent: Apr. 17, 2018

(54) PULSE WAVE MEASURING DEVICE (71) Applicants: DENSO CORPORATION, Kariya, Aichi-pref. (JP); Tsunemi Kanda, Nagakute, Aichi-pref. (JP); Satoshi Nakashima, Nagakute, Aichi-pref. (JP)

(72) Inventors: Kouki Futatsuyama, Kariya (JP); Tsunemi Kanda, Nagakute (JP); Satoshi Nakashima, Nagoya (JP)

(73) Assignees: DENSO CORPORATION, Kariya, Aichi-pref. (JP); Tsunemi Kanda, Nagakute, Aichi-Pref. (JP); Satoshi Nakashima, Nagakute, Aichi-Pref. (JP)

( * ) Notice: Subject to any disclaimer, the term of this patent is extended or adjusted under 35 U.S.C. 154(b) by 0 days.

(21) Appl. No.: 15/189,138

(22) Filed: Jun. 22, 2016

(65) Prior Publication Data

US 2017/0014038 A1   Jan. 19, 2017

(30) Foreign Application Priority Data

Jul. 14, 2015 (JP) .................. 2015-140421

(51) Int. Cl.
*A61B 5/00* (2006.01)
*A61B 5/024* (2006.01)

(52) U.S. Cl.
CPC ........ *A61B 5/02416* (2013.01); *A61B 5/6826* (2013.01); *A61B 5/6838* (2013.01); *A61B 2562/0233* (2013.01)

(58) Field of Classification Search
CPC . A61B 5/024; A61B 5/02416; A61B 5/02427; A61B 5/02433; A61B 5/6826; A61B 2562/0233–2562/0242
See application file for complete search history.

(56) References Cited

U.S. PATENT DOCUMENTS

2009/0143655 A1* 6/2009 Shani .................. A61B 5/0059
600/323
2014/0275949 A1 9/2014 Takahashi et al.

FOREIGN PATENT DOCUMENTS

| JP | H07-213498 A | 8/1995 |
| JP | H09-220207 A | 8/1997 |
| JP | 2014-180291 A | 9/2014 |

* cited by examiner

*Primary Examiner* — Scott Getzow
(74) *Attorney, Agent, or Firm* — Harness, Dickey & Pierce, P.L.C.

(57) ABSTRACT

A pulse wave measuring device includes a light emitter unit, a light receiver unit, a pulse wave measuring unit and a contact portion. The light receiver unit receives reflected light, which is reflected from a finger after transmission of the light from the light emitter unit. The pulse wave measuring unit measures a pulse wave based on the reflected light, which is received with the light receiver unit. The finger contacts the contact portion at a time of measuring the pulse wave. The contact portion has a recess, which receives at least a portion of the finger at the time of measuring the pulse wave, and a protrusion is provided in an inside of the recess.

21 Claims, 6 Drawing Sheets

PULSE WAVE MEASURING DEVICE

CROSS REFERENCE TO RELATED APPLICATION

This application is based on and incorporates herein by reference Japanese Patent Application No. 2015-140421 filed on Jul. 14, 2015.

TECHNICAL FIELD

The present disclosure relates to a pulse wave measuring device.

BACKGROUND

The following type of pulse wave measuring device has been known. Specifically, the known pulse wave measuring device includes a portion (hereinafter referred to as a contact portion), against which a fingertip of a user contacts at the time of measuring the pulse wave, a light emitting element and a light receiving element. The light emitting element emits the light to the fingertip that contacts the contact portion. The light receiving element receives a reflected light, which is reflected from the fingertip, or a transmitted light, which is transmitted through the fingertip. The pulse wave measuring device measures the pulse wave based on an oscillatory change in the amount of light that is received through the light receiving element (see, for example, JPH07-213498A).

In order to accurately measure the pulse wave, the fingertip needs to contact the contact portion with an appropriate pressing force. In the case of the previously proposed pulse wave measuring device, it is difficult for the user to sense a location of the contact portion, and the fingertip sometimes deviates from the contact portion. Furthermore, in the case of the previously proposed pulse wave measuring device, the pressing force for pressing the fingertip against the contact portion sometimes becomes excessively large or excessively small.

SUMMARY

The present disclosure is made in view of the above points. According to the present disclosure, there is provided a pulse wave measuring device that includes a light emitter unit, a light receiver unit, a pulse wave measuring unit and a contact portion. The light emitter unit emits light to a body part of a human body. The light receiver unit receives one of: reflected light that is a fraction of the light, which is emitted from the light emitter unit and is reflected from the body part; and transmitted light that is a fraction of the light, which is emitted from the light emitter unit and is transmitted through the body part. The pulse wave measuring unit measures a pulse wave based on the one of the reflected light and the transmitted light. The body part contacts against a contact portion at a time of measuring the pulse wave. The contact portion has a recess, which receives at least a portion of the body part at the time of measuring the pulse wave. A protrusion is provided in an inside of the recess.

BRIEF DESCRIPTION OF THE DRAWINGS

The drawings described herein are for illustration purposes only and are not intended to limit the scope of the present disclosure in any way.

DETAILED DESCRIPTION

Embodiments of the present disclosure will be described with reference to the accompanying drawings.

First Embodiment

1. Structure of Pulse Wave Measuring Device 1

Figure 1:
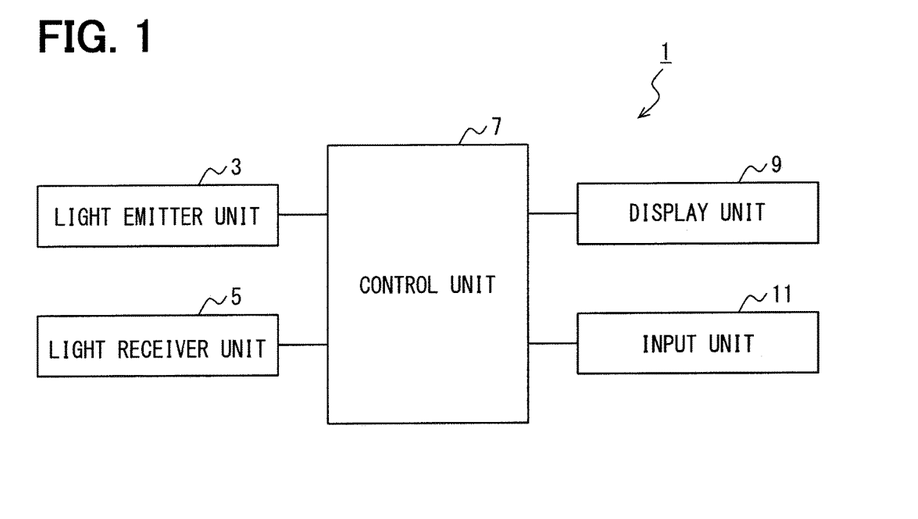
FIG. 1 is a block diagram showing an electrical construction of a pulse wave measuring device according to a first embodiment of the present disclosure.

A structure of a pulse wave measuring device 1 according to a first embodiment of the present disclosure will be described with reference to FIGS. 1 to 4. FIG. 1 shows an electrical construction of the pulse wave measuring device 1. The pulse wave measuring device 1 includes a light emitter unit 3, a light receiver unit 5, a control unit 7, a display unit 9 and an input unit 11.

The light emitter unit 3 is a light-emitting diode (LED) that emits green light in a wavelength of about 520 nm, which is the visible light, toward a finger of a user (an example of a body part of a human body of the present disclosure). The light receiver unit 5 is a photodiode (PD) that receives a reflected light that is a fraction of the light, which is emitted from the light emitter unit 3 and is reflected from the finger when the light is emitted from the light emitter unit 3. The reflected light includes a part of the light reflected from a blood vessel in an inside of the finger of the user. That is, when the light is emitted from the light emitter unit 3 toward the finger of the user, the light impinges on a small artery (arteriole) of the finger, which is referred to as a capillary artery, and a fraction of this light is absorbed by hemoglobin of blood flowing in the capillary artery, and a remaining fraction of this light is scattered at the capillary artery, and a part of this scattered light enters the light receiver unit 5.

The control unit 7 is a known computer (microcomputer) having, for example, a CPU, a RAM and a ROM. The control unit 7 runs a program stored in the ROM to execute a pulse wave measuring process described later. The control unit 7 measures the pulse wave based on the following principle. First of all, it should be noted that through use of the light receiver unit 5, the control unit 7 continuously obtains the amount of received light (hereinafter referred to as the received light amount) of the reflected light wave (or simply referred to as the reflected light).

The received light amount of the reflected light wave, which is reflected from the finger and is received by the light receiver unit 5, changes in an oscillatory pattern in response to the pulsation of the blood flow in the capillary artery. This is due to the following reason. Specifically, the pulsation of the blood flow causes that the amount of hemoglobin in the measurement location of the capillary artery changes in an oscillatory pattern, and thereby the amount of absorbed light, which is absorbed by the hemoglobin, also changes in an oscillatory pattern. The control unit 7 senses the oscillatory change in the received light amount of the reflected light wave as pulse wave information.

The display unit 9 is a liquid crystal display (LCD). The control unit 7 controls the display unit 9 to display a message, such as "MEASUREMENT OF PULSE WAVE HAS STARTED" or "MEASUREMENT OF PULSE WAVE HAS COMPLETED", which indicates a measurement state of the pulse wave, through the display unit 9. Furthermore, the control unit 7 controls the display unit 9 to display a result of the measurement of the pulse wave (e.g., "CURRENT HEART RATE IS 75 bpm").

The input unit 11 is a unit, through which user's input operation is applied. The input unit 11 has a touch panel.

Figure 2:
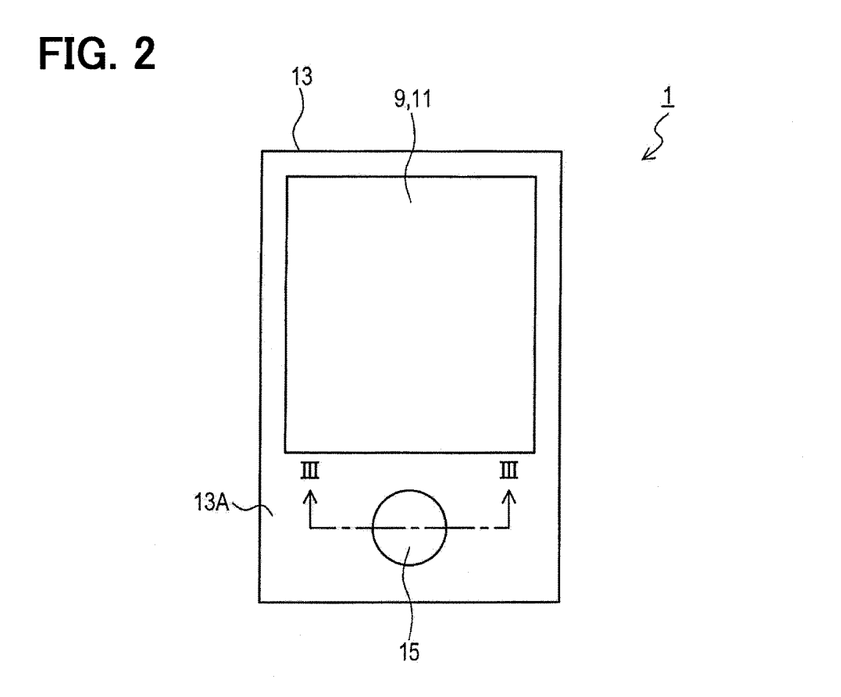
FIG. 2 is a front view of the pulse wave measuring device of the first embodiment.

As shown in FIG. 2, the pulse wave measuring device 1 includes a housing 13, which is shaped into a box form. The display unit 9 is installed in a front surface 13A of the housing 13. The input unit 11, which is the touch panel, is placed over a region of the display unit 9 to overlap with the display unit 9. A contact portion 15, against which the finger of the user contacts at the time of measuring the pulse wave, is formed in the front surface 13A.

Figure 3:
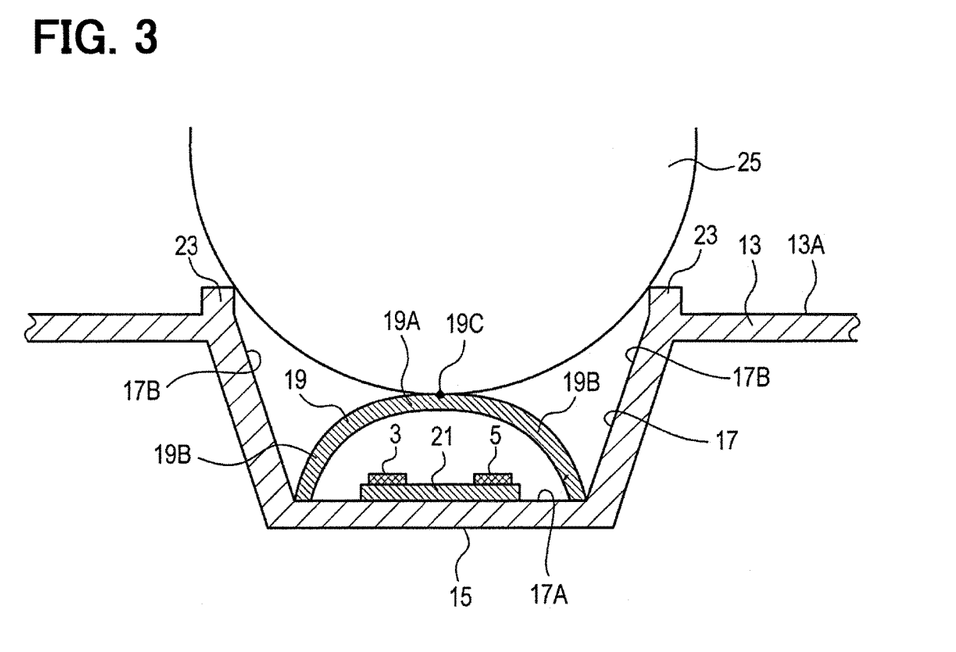
FIG. 3 is a cross sectional view taken along line in FIG. 2.
Figure 4:
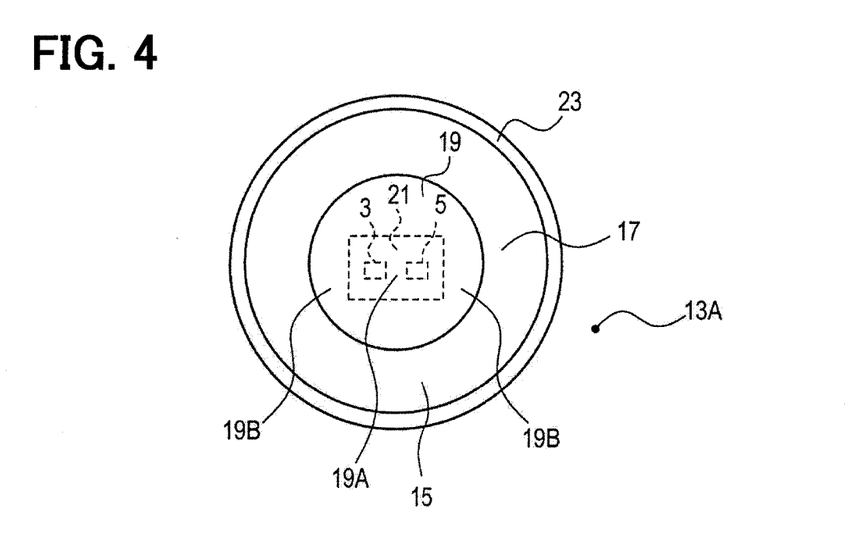
FIG. 4 is a front view of a contact portion of the pulse wave measuring device of the first embodiment.

As shown in FIGS. 3 and 4, the contact portion 15 has a recess 17. The recess 17 is a portion that is recessed from the other portion of the front surface 13A. A cross section of the recess 17 is tapered toward an inner side of the housing 13 (toward a bottom surface 17A of the recess 17) such that an inner diameter of the recess 17 is progressively reduced toward the inner side of the housing 13.

A lens 19 is installed in an inside of the recess 17. A cross section of the lens 19, which is taken along an imaginary plane that is perpendicular to the bottom surface 17A of the recess 17, is convex, i.e., is curved outwardly toward an upper side (toward an opening of the recess 17). A curvature of a center portion 19A of the cross section of the lens 19, which is curved outwardly toward the upper side, is smaller than a curvature of an outer peripheral portion 19B of the cross section of the lens 19. In a direction perpendicular to the bottom surface 17A of the recess 17, a location of an apex 19C of the lens 19 (a center of the center portion 19A of the lens 19) is lower than the front surface 13A (more specifically the portion of the front surface 13A, which is other than the recess 17 and a projection 23 described later). The bottom surface 17A of the recess 17 is covered with the lens 19, and an inner peripheral surface (side surface) 17B of the recess 17 is exposed from the lens 19.

A circuit board 21, the light emitter unit 3 and the light receiver unit 5 are received in an inside of the lens 19. In other words, the circuit board 21, the light emitter unit 3 and the light receiver unit 5 are placed on an inner side of the lens 19, which is opposite from the finger 25 in the direction perpendicular to the bottom surface 17A of the recess 17. The circuit board 21 holds the light emitter unit 3 and the light receiver unit 5.

The housing 13 has the projection (also referred to as a ridge or a rim) 23, which is formed along an outer periphery of the recess 17 in the front surface 13A. The projection 23 upwardly projects from the portion of the front surface 13A, which is located on a radially outer side of the projection 23. As shown in FIG. 4, the projection 23 is annular, i.e., is shaped into an annular ring form (a circular ring form) and circumferentially extends all around the recess 17. As shown in FIG. 3, when the finger 25 of the user contacts the contact portion 15, a portion of the finger 25 is received in the recess 17. The recess 17 has a circular shape when the recess 17 is viewed in a direction perpendicular to the front surface 13A.

The control unit 7 is an example of a pulse wave measuring unit of the present disclosure. The lens 19 is an example of a protrusion of the present disclosure, which is transparent.

2. Pulse Wave Measuring Process Executed by Pulse Wave Measuring Device 1

Figure 5:
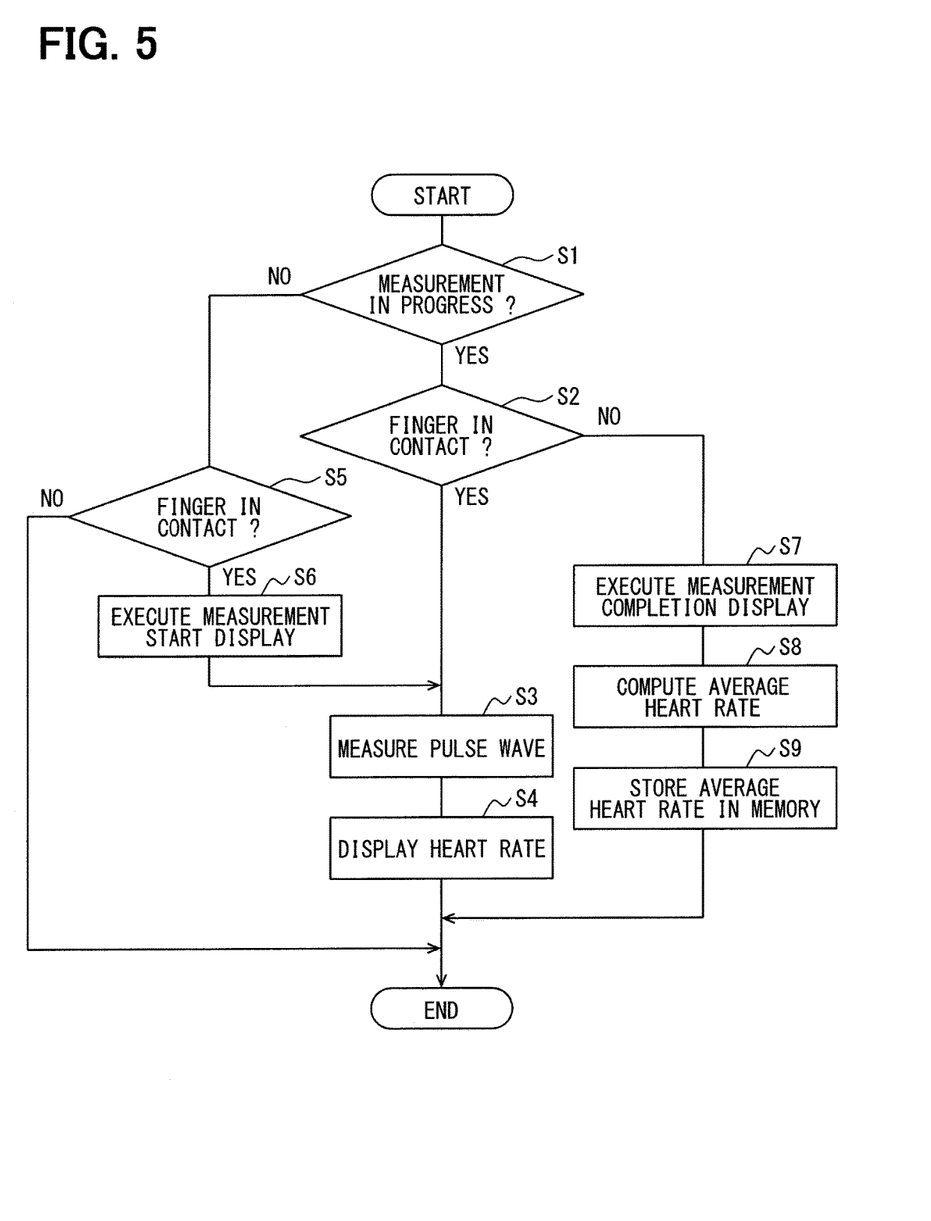
FIG. 5 is a flowchart indicating a pulse wave measuring process, which is executed by the pulse wave measuring device of the first embodiment.

A pulse wave measuring process, which is repeated by the pulse wave measuring device 1 (particularly the control unit 7) at predetermined time intervals, will be described with reference to a flowchart shown in FIG. 5. At step S1, it is determined whether the pulse wave measurement is in progress. The state, in which the pulse wave measurement is in progress, refers to a state, which is after execution of the measurement start display at step S6 and is before execution of the measurement completion display at step S7. When it is determined that the pulse wave measurement is in progress at step S1 (i.e., YES at step S1), the operation proceeds to step S2. In contrast, when it is determined that the pulse wave measurement is not in progress at step S1 (i.e., NO at step S1), the operation proceeds to step S5.

At step S2, it is determined whether the finger of the user is in contact with the contact portion 15. The control unit 7 may determine whether the finger of the user is in contact with the contact portion 15 based on a measurement signal of an undepicted contact sensor, which is installed in the contact portion 15. Alternatively, the control unit 7 may determine whether the finger of the user is in contact with the contact portion 15 based on the received amount of light, which is received by the light receiver unit 5. When it is determined that the finger of the user is in contact with the contact portion 15 at step S2 (i.e., YES at step S2), the operation proceeds to step S3. In contrast, when it is determined that the finger of the user is not in contact with the contact portion 15 at step S2 (i.e., NO at step S2), the operation proceeds to step S7.

At step S3, the pulse wave of the user is measured in the above-described manner.

Then, at step S4, the control unit 7 operates the display unit 9 to display the measured pulse wave, which is measured at step S3, as a heart rate on the display unit 9.

In contrast, when NO is returned at step S1, the operation proceeds to step S5. At step S5, the control unit 7 determines whether the finger of the user is in contact with the contact portion 15. The method of determining this is the same as that of step S2 described above. When it is determined that the finger of the user is in contact with the contact portion 15 at step S5 (i.e., YES at step S5), the operation proceeds to step S6. In contrast, when it is determined that the finger of the user is not in contact with the contact portion 15 at step S5 (i.e., NO at step S5), the process is terminated.

At step S6, the control unit 7 controls the display unit 9 to execute the measurement start display. The measurement start display may be, for example, the display of characters indicating "MEASUREMENT OF PULSE WAVE HAS STARTED" on the display unit 9. Thereafter, the operation proceeds to step S3.

When NO is returned at step S2, the operation proceeds to step S7. At step S7, the control unit 7 controls the display unit 9 to execute the measurement completion display. The measurement completion display may be, for example, the display of characters indicating "MEASUREMENT OF PULSE WAVE HAS COMPLETED" on the display unit 9.

At step S8, an average heart rate, which is an average of the heart rates measured from the time of starting the measurement of the pulse wave to the time of completing the measurement of the pulse wave, is computed.

At step S9, the computed average pulse rate, which is computed at step S8, is stored in a memory of the control unit 7.

3. Advantages of Pulse Wave Measuring Device 1

(1A) The pulse wave measuring device 1 has the recess 17, which can receive the portion of the finger 25. Therefore, the position of the finger 25 during the pulse wave measuring process is stabilized, and thereby reproducibility of the pulse wave measurement is improved. Furthermore, because of the presence of the recess 17, the user can easily sense a specified location, at which the finger 25 of the user needs to be placed during the pulse wave measurement.

(1B) The pulse wave measuring device 1 has the lens 19, which is shaped as the protrusion (shaped into the convex form). Since the lens 19 is in the form of the protrusion, the degree of contact between the finger 25 and the lens 19 is improved, and thereby a signal-to-noise ratio (SNR) at the pulse wave measurement is improved.

Furthermore, the lens 19, which is in the form of the protrusion, is placed in the recess 17. Therefore, in comparison to a case where the lens 19, which is in the form of the protrusion, is placed on the flat surface, it is possible to limit an excess increase in the contact pressure between the finger 25 and the lens 19. As a result, the SNR at the pulse wave measurement is improved. Particularly, since the location of the apex 19C of the lens 19 is lower than the portion of the front surface 13A (more specifically the portion of the front surface 13A, which is other than the recess 17 and the projection 23), the limiting effect for limiting the contact pressure between the finger 25 and the lens 19 is further enhanced.

(1C) The cross section of the lens 19 is curved outwardly toward the upper side. Therefore, the degree of contact between the finger 25 and the lens 19 is further improved.

(1D) The curvature of the center portion 19A of the lens 19 is smaller than the curvature of the outer peripheral portion 19B of the lens 19. Therefore, a contact surface area between the lens 19 and the finger 25 is increased, and thereby the SNR at the pulse wave measurement is improved. Furthermore, since the curvature at the center portion 19A is relatively small, it is possible to limit application of strong sensation to the finger 25.

(1E) The recess 17 is tapered. Therefore, even though the size of the finger 25 varies from person to person, the pulse wave measurement can be executed in a stable manner. For instance, in the case where the finger 25 is large, the finger 25 will contact only a shallow portion of the recess 17 and will not likely penetrate into a deep portion of the recess 17 at the time of inserting the finger 25 into the recess 17. In the case where the finger 25 is large, a thickness of the finger 25 is also large. Therefore, in general, the contact pressure of the finger 25 relative to the lens 19 tends to be excessively large. However, the insertion of the finger 25 is limited at the shallow portion of the recess 17, as discussed above, so that the contact pressure of the finger 25 relative to the lens 19 can be appropriately adjusted. As a result, the SNR at the pulse wave measurement is improved.

Furthermore, in a case where the finger 25 is small, the finger 25 can easily penetrate into the deep portion of the recess 17. In the case where the finger 25 is small, a thickness of the finger 25 is also small. Therefore, in general, the contact pressure of the finger 25 relative to the lens 19 tends to be excessively small. However, when the finger 25 is inserted into the deep portion of the recess 17, as discussed above, the contact pressure of the finger 25 relative to the lens 19 can be appropriately adjusted. As a result, the SNR at the pulse wave measurement is improved.

Furthermore, since the recess 17 has the tapered form, a degree of close contact between the finger 25 and the recess 17 (more specifically, the inner peripheral surface 17B of the recess 17) is increased, so that the ambient light will less likely enter into the lens 19. As a result, the SNR at the pulse wave measurement is improved.

(1F) The pulse wave measuring device 1 has the projection 23 around the recess 17. Thereby, the user can more easily sense the specified location, at which the finger 25 of the user needs to be placed during the pulse wave measurement. Furthermore, the projection 23 can limit intrusion of the ambient light into the inside of the recess 17. As a result, the SNR at the pulse wave measurement is improved.

(1G) The location of the apex 19C of the lens 19, which is shaped to protrude upwardly, is lower than the projection 23. Thereby, the user can easily sense the specified location, at which the finger 25 of the user needs to be placed during the pulse wave measurement. Furthermore, since the finger 25 itself is bulged (shaped to protrude), the contact between the lens 19, which is shaped to protrude upwardly, and the finger 25 can be appropriately maintained. Thus, the SNR of the pulse wave can be appropriately maintained.

(1H) In the view taken in the direction perpendicular to the front surface 13A, the recess 17 and the lens 19 have the circular shapes, respectively (see FIG. 4). Thereby, the stable measurement is possible without considering the contact direction of the finger 25. Furthermore, even if the way of holding the pulse wave measuring device 1 with the user's hand varies from person to person due to, for example, the size variation of the hand, the stable measurement is possible.

Second Embodiment

1. Structure of Pulse Wave Measuring Device 1

Figure 6:
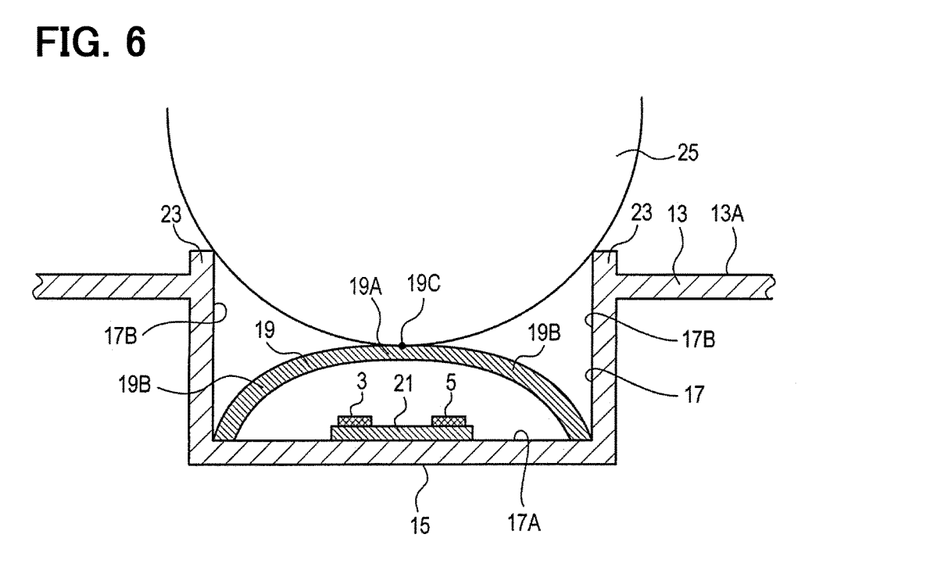
FIG. 6 is a cross sectional view that is similar to FIG. 3 and shows a cross section of a pulse wave measuring device according to a second embodiment of the present disclosure.

A basic structure of the pulse wave measuring device 1 according to a second embodiment of the present disclosure is the same as that of the first embodiment. Therefore, a common structure of the pulse wave measuring device 1, which is common to the first embodiment, will not be described for the sake of simplicity, and there will be mainly described only about a difference, which is different from the first embodiment. Specifically, as shown in FIG. 6, the recess 17 has a constant inner diameter along its entire depth extent regardless of the depth of the recess 17.

2. Pulse Wave Measuring Process Executed by Pulse Wave Measuring Device 1

The pulse wave measuring device 1 of the present embodiment executes the pulse wave measuring process, which is similar to that of the first embodiment.

3. Advantages of Pulse Wave Measuring Device 1

According to the second embodiment described above, the advantages (1A) to (1D), (1F), (1G) and (1H) of the first embodiment can be achieved.

Third Embodiment

1. Structure of Pulse Wave Measuring Device 1

Figure 7:
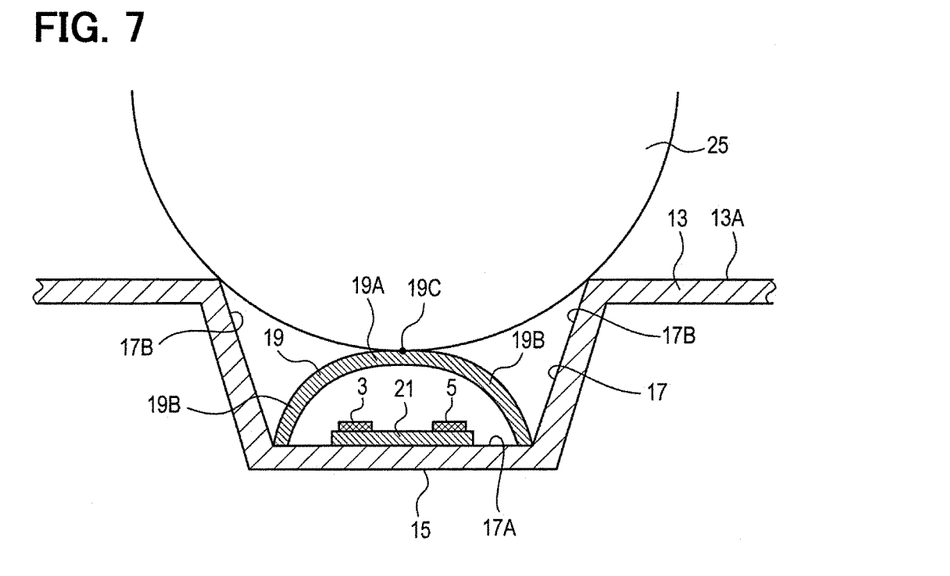
FIG. 7 is a cross sectional view that is similar to FIG. 3 and shows a cross section of a pulse wave measuring device according to a third embodiment of the present disclosure.

A basic structure of the pulse wave measuring device 1 according to a third embodiment of the present disclosure is the same as that of the first embodiment. Therefore, a common structure of the pulse wave measuring device 1, which is common to the first embodiment, will not be described for the sake of simplicity, and there will be mainly described only about a difference, which is different from the first embodiment. Specifically, as shown in FIG. 7, the housing 13 does not have the projection 23 of the first embodiment, and thereby the portion of the front surface 13A, which is located around the recess 17, is planar. The location of the apex 19C of the lens 19, which is shaped to protrude upwardly, is lower than the outer periphery of the recess 17, which is located on the radially outer side of the recess 17 in the front surface 13A.

2. Pulse Wave Measuring Process Executed by Pulse Wave Measuring Device 1

The pulse wave measuring device 1 of the present embodiment executes the pulse wave measuring process, which is similar to that of the first embodiment.

3. Advantages of Pulse Wave Measuring Device 1

According to the third embodiment described above, the following advantage can be achieved besides the advantages (1A) to (1E) and (1H) of the first embodiment.

(3A) The location of the apex 19C of the lens 19, which is shaped to project upward, is lower than the outer peripheral portion (the outer periphery) of the recess 17, which is located on the radially outer side of the recess 17 in the front surface 13A. Thereby, the user can easily sense the specified location, at which the finger 25 of the user needs to be placed during the pulse wave measurement. Furthermore, since the finger 25 itself is bulged (shaped to protrude), the contact between the lens 19, which is shaped to protrude upwardly, and the finger 25 is appropriately maintained. Thus, the SNR of the pulse wave can be appropriately maintained.

Fourth Embodiment

1. Structure of Pulse Wave Measuring Device 1

Figure 8:
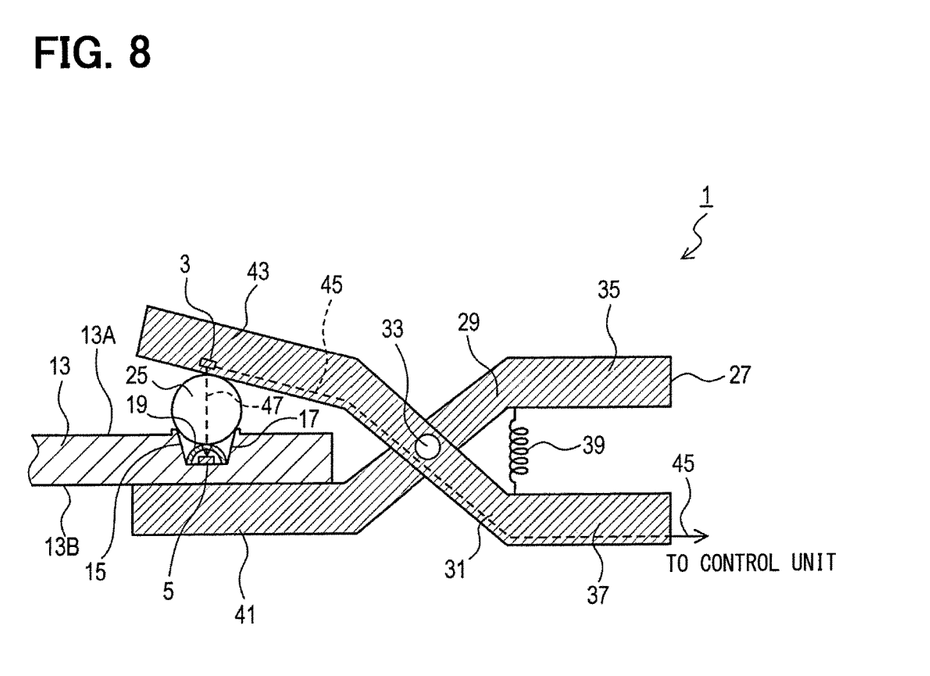
FIG. 8 is a cross sectional view that is similar to FIG. 3 and shows a cross section of a pulse wave measuring device according to a fourth embodiment of the present disclosure.

A basic structure of the pulse wave measuring device 1 according to a fourth embodiment of the present disclosure is the same as that of the first embodiment. Therefore, a common structure of the pulse wave measuring device 1, which is common to the first embodiment, will not be described for the sake of simplicity, and there will be mainly described only about differences, which are different from the first embodiment. As shown in FIG. 8, the pulse wave measuring device 1 has a clip 27 in addition to the main body received in the housing 13. The clip 27 includes a first member 29 and a second member 31, which are rotatably coupled together by a rotation shaft 33. Furthermore, the clip 27 has a spring 39 that urges a manipulating portion 35 of the first member 29 and a manipulating portion 37 of the second member 31 away from each other. A distal end portion 41 of the first member 29 and a distal end portion 43 of the second member 31 receive a force, which is exerted by the spring 39 to urge the distal end portion 41 of the first member 29 and the distal end portion 43 of the second member 31 toward each other. When the user grips the manipulating portions 35, 37 and forces the manipulating portions 35, 37 toward each other, the distal end portions 41, 43 move away from each other. When the user releases the manipulating portions 35, 37, the distal end portions 41, 43 are urged toward each other by the resilient force of the spring 39 and thereby contact with each other.

In the present embodiment, the light emitter unit 3 is installed at the distal end portion 43. The light emitter unit 3 and the control unit 7 are interconnected by a signal line 45. Similar to the first embodiment, the light receiver unit 5 is received in the inside of the lens 19.

At the time of measuring the pulse wave, as shown in FIG. 8, the housing 13 and the finger 25 are clamped between the distal end portions 41, 43 of the clip 27. At this time, the finger 25 contacts the contact portion 15 of the housing 13. The clip 27 is oriented such that the distal end portion 43 contacts the finger 25, and the distal end portion 41 contacts a back surface 13B of the housing 13.

The light 47, which is emitted from the light emitter unit 3, penetrates through the finger 25 and enters the light receiver unit 5. At this time, a portion of the light 47 impinges on the small artery (capillary artery) of the finger 25, and a fraction of this impinged light is absorbed by hemoglobin of blood flowing in the capillary artery, and a remaining fraction of this impinged light enters the light receiver unit 5. The received light amount of light (transmitted light that is transmitted through the finger), which enters the light receiver unit 5, changes in an oscillatory pattern in response to the pulsation of the blood flow in the capillary artery. This is due to the following reason. Specifically, the pulsation of the blood flow causes that the amount of hemoglobin at the measurement location of the capillary artery changes in an oscillatory pattern, and thereby the amount of absorbed light, which is absorbed by the hemoglobin, also changes in an oscillatory pattern. The control unit 7 senses the oscillatory change in the received light amount of the transmitted light, which is transmitted through the finger 25 and is received by the light receiver unit 5, as pulse wave information.

2. Pulse Wave Measuring Process Executed by Pulse Wave Measuring Device 1

The pulse wave measuring device 1 of the present embodiment executes the pulse wave measuring process, which is similar to that of the first embodiment.

3. Advantages of Pulse Wave Measuring Device 1

According to the fourth embodiment described above, the advantages (1A) to (1H) of the first embodiment can be achieved.

Other Embodiments

The embodiments of the present disclosure have been described. However, the present disclosure should not be limited to the above embodiments, and the above embodiments may be modified within the principle of the present disclosure.

(1) The body part of the user, which is used to measure the pulse wave, may be another body part (e.g., a palm, an ear, a leg), which is other than the finger.

(2) In the second embodiment, the projection 23 may be eliminated from the housing 13.

(3) In the fourth embodiment, the configuration of the recess 17 may be modified to the configuration of the recess 17 of the second embodiment. Furthermore, in the fourth embodiment, the projection 23 may be eliminated from the housing 13.

(4) In the first to fourth embodiments, the curvature of the center portion 19A of the lens 19 may be the same as the curvature of the outer peripheral portion 19B.

(5) In the fourth embodiment, the light receiver unit 5 may be installed to the distal end portion 43, and the light emitter unit 3 may be placed in the inside of the lens 19.

(6) In the first, second and fourth embodiments, the projection 23 may be formed only in a portion(s) of the outer periphery of the recess 17. For instance, a plurality of projections, which may be fragments of the annular projection 23 of the first embodiment, may be intermittently formed along the outer periphery of the recess 17.

(7) The function(s) of any one of the constituent components of the pulse wave measuring device of any one of the above embodiments may be carried out by a plurality of constituent components. Also, the functions of two or more of the constituent components of the pulse wave measuring device of any one of the above embodiments may be consolidated into and carried out by one constituent component. At least one of the constituent components of the pulse wave measuring device of any one of the above embodiments may be replaced with a known component (or a known structure) having the same or similar function, which is the same or similar to the function of the at least one of the constituent components. Furthermore, one of the constituent components of the pulse wave measuring device of any one of the above embodiments may be eliminated. Furthermore, at least one of the constituent components of the pulse wave measuring device of any one of the above embodiments may be added to the pulse wave measuring device of another one of the above embodiments or may be replaced with at least one of the constituent components of the pulse wave measuring device of another one of the above embodiments. Furthermore, any aspect encompassed by the technical idea, which is specified by the limitations of claim(s) of the present application, should serve as an embodiment of the present disclosure.

(8) Besides the pulse wave measuring device described above, the present disclosure may be embodied in various other ways, such as a system, which includes the pulse wave measuring device as a constituent component of the system, a program for functioning a computer as the control unit of the pulse wave measuring device, a storage medium, which stores such a program, and/or a pulse wave measuring method.

Figure 9:
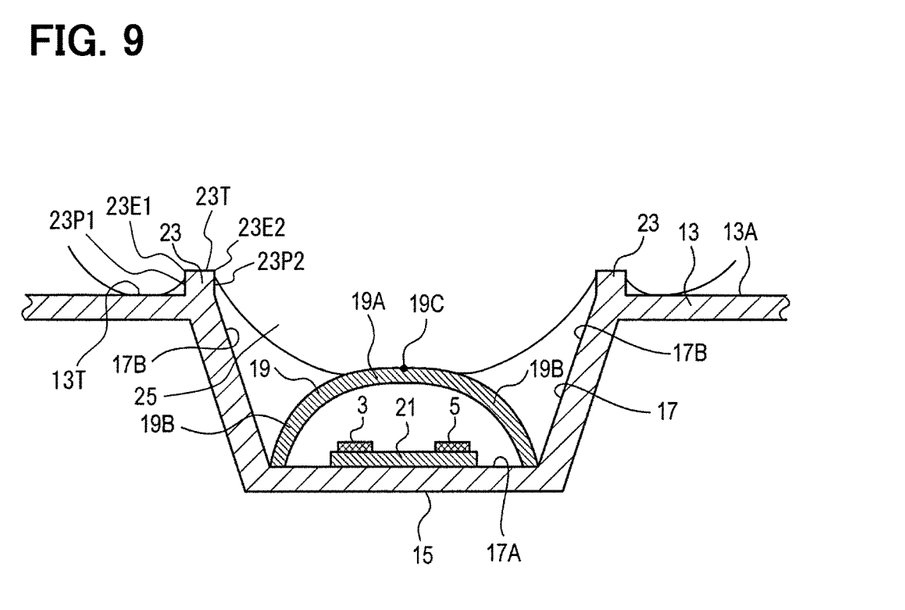
FIG. 9 is a cross sectional view similar to FIG. 3, indicating a modification of the first embodiment.

(9) FIG. 3 of the first embodiment illustrates that the finger 25 of the user contacts the projection 23, which is shaped into the annular ring form (the circular ring form), and the center portion 19A of the lens 19 at the time of measuring the pulse wave of the finger 25. Alternatively, at the time of measuring the pulse wave, the finger 25 may be placed to contact an adjacent location 13T of the front surface 13A of the housing 13, which is located on a radially outer side of the projection 23, as indicated in FIG. 9. In the case of FIG. 9, besides the adjacent location 13T of the front surface 13A and the center portion 19A of the lens 19, the finger 25 contacts a cylindrical outer peripheral surface 23P1, a right-angled outer peripheral edge 23E1, a flat top surface 23T, a right-angled inner peripheral edge 23E2 and a cylindrical inner peripheral surface 23P2 of the projection 23. The adjacent location 13T of the front surface 13A extends linearly in the left-to-right direction and circumferentially continuously extends all around the projection 23 as a ring-shaped flat surface. Each of the outer peripheral surface 23P1 and the inner peripheral surface 23P2 extends linearly in the top-to-bottom direction (the direction perpendicular to the left-to-right direction) and circumferentially continuously extends all around the projection 23. Each of the outer peripheral edge 23E1 and the inner peripheral edge 23E2 has a right angle in the cross section shown in FIG. 9 and circumferentially continuously extends all around the projection 23. Additionally, the top surface 23T extends linearly in the left-to-right direction and circumferentially continuously extends all around the projection 23 as a ring-shaped flat surface.

When the number of tactile stimuli, which are applied from the contact portion 15 of the pulse wave measuring device 1 to the finger 25 of the user, is increased, the user can more appropriately position the finger 25 relative to the center of the contact portion 15 (the center of the projection 23 where the apex 19C of the lens 19 is located). Particularly, in the case of FIG. 9, the adjacent location 13T of the front surface 13A, the outer peripheral surface 23P1, the outer peripheral edge 23E1, the top surface 23T, the inner peripheral edge 23E2 and the inner peripheral surface 23P2 of the projection 23 extend circumferentially continuously all around the projection 23. Therefore, the finger 25 can contact these parts 13T, 23P1, 23E1, 23T, 23E2, 23P2 along the entire circumferential extent of the projection 23 to receive the tactile stimuli. Thus, the user can more easily place the finger 25 at the center of the contact portion 15 by sensing these tactile stimuli in comparison to, for example, the pulse wave measuring device 1 of FIG. 7 where the projection 23 is eliminate. Particularly, the geometrical differences of these parts 13T, 23P1, 23E1, 23T, 23E2, 23P2 can provide different tactile stimuli to the finger 25 of the user. These different tactile stimuli are applied to the finger 25 one after another at the time of placing the finger 25 onto the contact portion 15.

In order to enable the user to place the finger 25 in place, it is desirable to provide at least three tactile stimuli (specifically, the tactile stimuli applied from the outer peripheral edge 23E1, the top surface 23T and the inner peripheral edge 23E2) to the finger 25 of the user besides the tactile stimulus from the center portion 19A of the lens 19. Alternatively, in order to further improve positioning accuracy of the finger 25, it is desirable to provide at least five tactile stimuli (specifically, the tactile stimuli applied from the outer peripheral surface 23P1, the outer peripheral edge 23E1, the top surface 23T, the inner peripheral edge 23E2 and the inner peripheral surface 23P2) to the finger 25 of the user besides the tactile stimulus from the center portion 19A of the lens 19. However, the number of tactile stimuli is not limited to these numbers and may be changed to any other number. Also, the angle of each of the outer peripheral edge 23E1 and the inner peripheral edge 23E2 is not limited to the right angle and may be changed to an acute angle or an obtuse angle.

Furthermore, in the first, second and fourth embodiments, although the projection 23 is shaped into the annular ring form (the circular ring form), the shape of the projection 23 should not be limited to the circular ring form. That is, the projection 23 may be formed into any other ring form, such as a polygonal ring form (e.g., a triangular ring form, a square ring form, a pentagonal ring form, a hexagonal ring form or the like) or a curved ring form (e.g., an oblong ring form, an oval ring form, an ellipse ring form or the like) other than the annular ring form (the circular ring form). In such a case, the shape of the recess 17, which is seen from the top side of the recess 17 and is indicated in FIG. 4, may be changed from the circular form to a corresponding form (e.g., a polygonal form or a curved form) that corresponds to the shape of the projection 23 discussed above. Also, a plurality of projections, which may be fragments of the ring form of the projection 23 discussed above, may be intermittently formed along the outer periphery of the recess 17 in place of projection 23 shaped into the ring form.

What is claimed is:

1. A pulse wave measuring device comprising:
a light emitter unit that emits light to a body part of a human body;
a light receiver unit that receives one of:
reflected light that is a fraction of the light, which is emitted from the light emitter unit and is reflected from the body part; and
transmitted light that is a fraction of the light, which is emitted from the light emitter unit and is transmitted through the body part;
a pulse wave measuring unit that measures a pulse wave based on the one of the reflected light and the transmitted light; and
a contact portion, against which the body part contacts at a time of measuring the pulse wave, wherein:
the contact portion has a recess, which receives at least a portion of the body part at the time of measuring the pulse wave, and a protrusion is provided in an inside of the recess;
the light receiver unit receives the reflected light;
the protrusion is transparent; and
the light emitter unit and the light receiver unit are placed on an inner side of the protrusion, which is opposite from the body part.

2. The pulse wave measuring device according to claim 1, wherein a cross section of the protrusion is curved outwardly toward an upper side.

3. The pulse wave measuring device according to claim 2, wherein a curvature of a center portion of the cross section of the protrusion is smaller than a curvature of an outer peripheral portion of the cross section of the protrusion.

4. The pulse wave measuring device according to claim 1, wherein a cross section of the recess is tapered.

5. The pulse wave measuring device according to claim 1, wherein a projection is formed along an outer periphery of the recess.

6. The pulse wave measuring device according to claim 1, wherein the protrusion is lower than an outer periphery of the recess.

7. The pulse wave measuring device according to claim 5, wherein the protrusion is lower than the projection.

8. The pulse wave measuring device according to claim 5, wherein:
the projection is shaped into a ring form; and
the projection has a flat top surface.

9. The pulse wave measuring device according to claim 8, wherein the projection has a cylindrical outer peripheral surface and a cylindrical inner peripheral surface.

10. The pulse wave measuring device according to claim 9, wherein:
a right-angled outer peripheral edge is formed between the flat top surface and the cylindrical outer peripheral surface; and
a right-angled inner peripheral edge is formed between the flat top surface and the cylindrical inner peripheral surface.

11. A pulse wave measuring device comprising:
a light emitter unit that emits light to a body part of a human body;
a light receiver unit that is installed on a circuit board and receives one of:
reflected light that is a fraction of the light, which is emitted from the light emitter unit and is reflected from the body part; and
transmitted light that is a fraction of the light, which is emitted from the light emitter unit and is transmitted through the body part;
a pulse wave measuring unit that measures a pulse wave based on the one of the reflected light and the transmitted light; and
a contact portion, against which the body part contacts at a time of measuring the pulse wave, wherein:
the contact portion has a recess, which receives at least a portion of the body part at the time of measuring the pulse wave, and a protrusion is provided in an inside of the recess, and
an opening of the recess opens in a direction that is perpendicular to a plane of the circuit board.

12. The pulse wave measuring device according to claim 11, wherein a cross section of the protrusion is curved outwardly toward an upper side where the opening of the recess is located.

13. The pulse wave measuring device according to claim 12, wherein a curvature of a center portion of the cross section of the protrusion is smaller than a curvature of an outer peripheral portion of the cross section of the protrusion.

14. The pulse wave measuring device according to claim 11, wherein a cross section of the recess is tapered.

15. The pulse wave measuring device according to claim 11, wherein a projection is formed along an outer periphery of the recess.

16. The pulse wave measuring device according to claim 11, wherein the protrusion is lower than an outer periphery of the recess.

17. The pulse wave measuring device according to claim 15, wherein the protrusion is lower than the projection.

18. The pulse wave measuring device according to claim 15, wherein:
the projection is shaped into a ring form; and
the projection has a flat top surface.

19. The pulse wave measuring device according to claim 18, wherein the projection has a cylindrical outer peripheral surface and a cylindrical inner peripheral surface.

20. The pulse wave measuring device according to claim 19, wherein:
a right-angled outer peripheral edge is formed between the flat top surface and the cylindrical outer peripheral surface; and
a right-angled inner peripheral edge is formed between the flat top surface and the cylindrical inner peripheral surface.

21. The pulse wave measuring device according to claim 11, wherein:
the light receiver unit receives the reflected light;
the protrusion is transparent; and
the light emitter unit and the light receiver unit are placed on an inner side of the protrusion, which is opposite from the body part.

* * * * *